United States Patent [19]

Boss et al.

[11] Patent Number: 4,816,397

[45] Date of Patent: Mar. 28, 1989

[54] MULTICHAIN POLYPEPTIDES OR PROTEINS AND PROCESSES FOR THEIR PRODUCTION

[75] Inventors: Michael A. Boss, Slough; John H. Kenten; John S. Emtage, both of High Wycombe; Clive R. Wood, Near Fordingbridge, all of United Kingdom

[73] Assignee: Celltech, Limited, Slough, United Kingdom

[21] Appl. No.: 672,265

[22] PCT Filed: Mar. 23, 1984

[86] PCT No.: PCT/GB84/00094

§ 371 Date: Nov. 14, 1984

§ 102(e) Date: Nov. 14, 1984

[87] PCT Pub. No.: WO84/03712

PCT Pub. Date: Sep. 27, 1984

[30] Foreign Application Priority Data

Mar. 25, 1983 [GB] United Kingdom ............... 8308235

[51] Int. Cl.⁴ .................. C12P 21/00; C12N 15/00; C12N 1/00; C12N 1/20

[52] U.S. Cl. .................. 435/68; 435/172.3; 435/243; 435/255; 435/320; 435/252.31; 435/252.33

[58] Field of Search .............. 435/68, 172.3, 243, 435/320, 253, 255

[56] References Cited

U.S. PATENT DOCUMENTS

4,403,036 9/1983 Hartley et al. .................. 435/68
4,642,334 2/1987 Moore et al. .................. 435/68

FOREIGN PATENT DOCUMENTS

037723 10/1981 European Pat. Off. .
041313 12/1981 European Pat. Off. .
041767 12/1981 European Pat. Off. .
055945 7/1982 European Pat. Off. .
075444 3/1983 European Pat. Off. .
088994 9/1983 European Pat. Off. .
0125023 11/1984 European Pat. Off. .

OTHER PUBLICATIONS

Adams et al., Biochemistry, vol. 19, pp. 2711-2719, 1980.
Haley et al., DNA, vol. 1, pp. 155-162, 1982.
Gough et al., Biochemistry, vol. 19, pp. 2702-2710, 1980.
Iserentant et al., Gene, vol. 9, pp. 1-12, 1980.
Seidman et al: "Immunoglobulin light-chain structural gene sequences cloned in a bacterial plasmid," *Nature*, vol. 271, pp. 582-585, 1978.

*Primary Examiner*—Blondel Hazel
*Attorney, Agent, or Firm*—Cushman, Darby & Cushman

[57] ABSTRACT

Multichain polypeptides or proteins and processes for their production in cells of host organisms which have been transformed by recombinant DNA techniques. According to a first aspect of the present invention, there is provided a process for producing a heterologous multichain polypeptide or protein in a single host cell, which comprises transforming the host cell with DNA sequences coding for each of the polypeptide chains and expressing said polypeptide chains in said transformed host cell. According to another aspect of the present invention there is provided as a product of recombinant DNA technology an Ig heavy or light chain or fragment thereof having an intact variable domain. The invention also provides a process for increasing the level of protein expression in a transformed host cell and vectors and transformed host cells for use in the processes.

18 Claims, 13 Drawing Sheets

Possible 2° structures of μ mRNAs

5'→3' pNP9.    ΔG = 7.6 K.cal.
(1.0 ru)

pNP11.    ΔG=7.8 Kcal.
(6.9ru)

pNP12    ΔG= 7.6 Kcal.
(1.8 ru)

pNP14.                          (101.2 ru)

-AAGGGUAUGAUCA AUG CAAGUGCAACUGCAG

Binding of antibodies to NIP-cap BSA
B1-8 IgM (■), fraction 26 (▲),
purified Ig μ or λ (●), in the presence
of free NIP-cap (----) or NIP-cap (———).

MULTICHAIN POLYPEPTIDES OR PROTEINS AND PROCESSES FOR THEIR PRODUCTION

This invention relates to multichain polypeptides or proteins and processes for their production in cells of host organisms which have been transformed by recombinant DNA techniques.

In recent years advances in molecular biology based on recombinant DNA techniques have provided processes for the production of heterologous (foreign) polypeptides or proteins in host cells which have been transformed with heterologous DNA sequences which code for the production of these products.

Theoretically, the recombinant DNA approach may be applied to the production of any heterologous polypeptide or protein in a suitable host cell, provided that appropriate DNA coding sequences can be identified and used to transform the host cell. In practice, when the recombinant DNA approach was first applied to the production of commercially useful products, its application for the production of any specified polypeptide or protein presented particular problems and difficulties, and the success of applying this approach to the production of any particular polypeptide or product was not readily predictable.

However, a large number of heterologous single chain polypeptides or proteins have now been produced by host cells transformed by recombinant DNA techniques. Examples of such heterologous single chain polypeptides or proteins include human interferons, the A and B chains of human insulin, human and bovine growth hormone, somatostatin, calf prochymosin and urokinase. Such transformed host cells provide a reproducible supply of authentic heterologous polypeptiede or protein which may be produced on an industrial scale using industrial fermentation technology.

It should be pointed out that some of these polypeptides, for instance urokinase, after secretion by a host cell appear as two chain molecules. However, in such cases, the molecule is synthesised by the host cell as a single chain polypeptide, coded for by a single DNA sequence, which is cleaved in the host cell subsequent to synthesis to form the two chain structure.

It is known that in both human and animal systems there are a number of polypeptides or proteins which have multichain structure in which the chains are not derived from the cleavage of a single chain polypeptide coded for by a single DNA sequence. In such cases, the gene for each of the chains may be located at different points on the same chromosome or even on different chromosomes. In these cases, the polypeptide chains are synthesised separately and then assembled into the complete molecule subsequent to synthesis. Heretofore, no such multichain polypeptide or protein has been produced by recombinant DNA techniques from a single host cell.

A particular example of a class of such multichain polypeptides or proteins is the immunoglobulins.

Immunoglobulins, commonly referred to as antibodies, are protein molecules produced in animals by B-lymphocyte cells in response to challenge with foreign antigenic agents, such as bacteria, viruses and foreign proteins. The immunoglobulins comprise a crucial part of the immune systems of humans and animals. The immunoglobulins recognise specific parts of the foreign agents and bind onto them. The specific parts are usually known as antigenic determinants or antibody binding sites. A given foreign agent is likely to have a number of different antigenic determinants.

A typical immunoglobulin (Ig) molecule is shown in FIG. 1 of the accompanying drawings, to which reference is now made. The Ig molecule comprises two identical polypeptide chains of about 600 amino acid residues (usually referred to as the heavy chains H), disulphide bonded to each other, and two identical shorter polypeptide chains of about 220 amino acid residues (usually referred to as the light chains L), each light chain being disulphide bonded to one end of each heavy chain as shown.

When the Ig molecule is correctly folded, each chain is formed into a number of distinct globular areas, usually known as domains, joined by a more linear polypeptide chain. The light chains have two such domains, one of which is of variable sequence $V_L$, and the other of which is of constant sequence $C_L$. The heavy chains have a single variable domain $V_H$ adjacent the variable domain $V_L$ of the light chain, and three or four constant domains $C_{H1-3 \, or \, 4}$.

The variable domains on both the heavy and the light chains each contain three hypervariable regions (HV1-3) which, when the Ig molecule is correctly folded, are located adjacent one another and form the antigen binding site. It is this area which recognises and binds to the antigenic determinant for which the Ig molecule is specific.

The constant domains of the Ig molecule do not take part in the binding to the antigenic determinant, but mediate the actions triggered by the binding of the Ig molecule to the antigenic determinant. It is believed that this triggering is caused by an allosteric effect induced by the binding of the Ig molecule to the antigenic determinant. The constant domain may enable the Ig molecule to fix complement or may cause mast cells to release histamine.

Ig's may be categorised by class or subclass, depending on which of a number of possible heavy chain constant domains they contain, there being eight such possible heavy chains in mice. Thus, for instance, and Ig molecule with a $\mu$ heavy chain belongs to the class IgM, and one with a $\gamma_1$ heavy chain to the class IgG$_1$.

Ig's may also contain one of two light chains, designated as $\kappa$ and $\lambda$ light chains, which have different constant domains and different sets of variable domains.

The structure of the Ig molecule and the location of the genes coding for the various domains thereof are discussed more fully by Early and Hood, in Genetic Engineering, Principles and Methods, Vol. 3, pages 153-158 (edited by Setlow and Hollaender, Plenum Press).

It is known that Ig molecules on digestion with selected enzymes can produce a number of immunologically functional fragments. Two such fragments are known as the $F_{ab}$ and $(F_{ab}')_2$ fragments. The $F_{ab}$ fragment comprises one light chain linked to the $V_H$ and $C_{H1}$ domains of a heavy chain as shown in FIG. 1. The $(F_{ab}')_2$ fragment consists essentially of two $F_{ab}$ fragments linked together by a small additional portion of the heavy chains as shown in FIG. 1. These fragments and other similar fragments can be of use in various tests and diagnostic and medical methods.

The principle method employed for the production of Ig's involves the immunisation of susceptible animals with the antigenic agent to provide an immune reaction. Generally the animal is immunised a second time to improve the yield of Ig. The animal is then bled and the Ig is recovered from the serum.

However, the product of this method is not a homogeneous protein. The animal will produce Ig of different classes and also Ig specific for each of the different antigenic determinants on the antigenic agent, and its blood will therefore contain a heterogeneous mixture of Ig's. Obtaining a specific Ig of particular class and desired specificity from such a mixture requires very difficult and tedious purification procedures.

Recently, it has become possible to produce a homogeneous Ig of a single class and a single specificity by a technique first described by Kohler and Milstein (Nature, 256, 495-479, 1975). The technique involves the fusion of single Ig-producing parent cells with cancer cells to produce a monoclonal hybridoma cell which produces the Ig. Ig produced by this technique is usually known as monoclonal antibody. The nature of the monoclonal Ig is determined by the class and specificity of the Ig produced by the parent cell.

Recently attempts have been made to use recombinant DNA techniques to produce fragments of Ig molecules. For instance, Amster et al. (Nucleic Acid Research, 8, No. 9, 1980, pp 2055 to 2065) disclose the cloning of double stranded cDNA sequences encoding for a mouse Ig light chain into a plasmid. An E. Coli strain transformed by the plasmid synthesised a protein thought to comprise the complete constant domain of the light chain and about 40 amino acid residues of its variable region.

Kemp and Cowman (Proc. Natl. Acad. Sci. USA, 78, 1981, pp 4520 to 4524) disclose the cloning of cDNA sequences encoding for mouse heavy chain fragments and the transforming of an E. Coli strain which then synthesised heavy chain polypeptide fragments.

In both these cases, the polypeptides were produced as fusion proteins, in which the fragments of the Ig polypeptides were fused with additional non-Ig polypeptide sequences, and the incomplete variable domains. Thus, the polypeptide chains produced in these studies were not immunologically functional polypeptides as they were incapable of combining with complementary heavy or light chains to provide Ig molecules having intact antigen binding sites and immunological function.

Research studies have also been carried out in mammalian systems. For instance, Falkner and Zachau (Nature, 298, 1982, pp 286 to 288) report the cloning of cDNA sequences encoding for mouse light chains into a plasmid which was used to transfect genomic eukaryotic cells which could then transiently synthesise light chains.

Rice and Baltimore (Proc. Natl. Acad. Sci. USA, 79, 1982, pp 7862 to 7865) report on the transfection of a functionally rearranged K light chain Ig gene into a murine leukemia virus-transformed lymphoid cell line. The cell line is then able to express the gene continuously. In both these cases, the K genes used to transfect the mammalian cells were obtained from myeloma cells and the K polypeptides produced were of indeterminate immunological function.

A further approach is exemplified in a series of papers by Valle et al. (Nature, 291, 1981, 338-340; Nature, 300, 1982, 71-74 and J. Mol. Biol., 160, 1982, 459-474), which describe the microinjection of mRNAs encoding for heavy or light chains of Ig isolated from a mouse myeloma line into oocytes of Xenopus laevis. Under certain conditions complete Ig molecules were formed. However, the mRNAs were obtained from myeloma cells and the Ig molecules were of indeterminate immunological function.

It can thus be seen that hitherto it has not been possible to produce functional Ig by recombinant DNA technology.

According to a first aspect of the present invention, there is provided a process for producing a heterologous multichain polypeptide or protein in a single host cell, which comprises transforming the host cell with DNA sequences coding for each of the polypeptide chains and expressing said polypeptide chains in said transformed host cell.

According to a second aspect of the present invention, there is provided a heterologous multichain polypeptide or protein produced by recombinant DNA technology from a single host cell.

The present invention is of particular, but not exclusive, application in the production of Ig molecules and immunologically functional Ig fragments of the type referred to above. However, it will be appreciated that the present invention can be applied to the production of other multichain polypeptides or proteins.

In relation to the product of Ig molecules according to the invention it will be appreciated that, in order to produce a functional molecule, the DNA sequences used to transform the host cell will need to encode for at least the $V_L$ and $V_H$ domains of an Ig molecule. Moreover, these domains will need to be complementary so that when the two polypeptide chains fold together they form an antigen binding site of predetermined specificity.

Preferably, the Ig molecule or fragment include a complete light chain and at least the $C_{H1}$ domain in addition to the $V_H$ domain of the heavy chain. Most preferably the Ig molecule is intact.

It has also been shown by the present applicants that it is now possible to produce individual heavy and light chains having intact variable domains. This has not previously been possible. Therefore, according to a third aspect of the present invention there is provided as a product of recombinant DNA technology an Ig heavy or light chain or fragment thereof having an intact variable domain.

Advantageously, the Ig molecule or functional fragment thereof according to the present invention has a variable region (formed by the $V_L$ and $V_H$ domains) which defines a binding site for an antigenic determinant of clinical or industrial importance. The DNA coding sequences necessary to produce such a molecule may be derived from naturally occuring or hybridoma (monoclonal)Ig-producing cells with the desired specificity.

The constant domains of the Ig molecule or fragment, if present, may be derived from the same cell line as the variable region. However, the constant domains may be specifically altered, partially or completely omitted, or derived from a cell line producing a different class of Ig to provide Ig molecules or fragments having desired properties.

For example, an Ig molecule may be produced having variable domains ($V_H$ and $V_L$) identical with those from a monoclonal antibody having a desired specificity, and constant domain(s) from a different monoclonal antibody having desired properties, for instance to provide human compatibility or to provide a complement binding site.

Such alterations in the amino acid sequence of the constant domains may be achieved by suitable mutation or partial synthesis and replacement or partial or complete substitution of appropriate regions of the corresponding DNA coding sequences. Substitute constant domain portions may be obtained from compatible recombinant DNA sequences.

The invention may be utilised for the production of Ig molecules or fragments useful for immunopurification, immunoassays, cytochemical labelling and targeting methods, and methods of diagnosis or therapy. For example, the Ig molecule or fragment may bind to a therapeutically active protein such as interferon or a blood clotting factor, for example Factor VIII, and may therefore be used to produce an affinity chromatorgraphy medium for use in the immunopurification or assay of the protein.

It is also envisaged that the Ig molecule may be synthesised by a host cell with another peptide moiety attached to one of its constant domains. Such a further peptide moiety may be cytotoxic or enzymatic. Alternatively, the moiety may be useful in attaching the Ig molecule to a biological substrate, such a cell or tissue, or to a non-biological substrate, such as a chromatography medium. Such a peptide moiety is herein referred to as a structural peptide moiety.

It is further envisaged that cytotoxic, enzymic or structural peptide moieties could be attached to the Ig molecule by normal peptide chemical methods, as are already known in the art, rather than by being synthesised with the Ig molecule.

The Ig molecule or fragment may also comprise a therapeutic agent in its own right. For instance, an Ig molecule or fragment specific for D blood group antigen may be useful for the prevention of haemolytic disease of the new born.

Any suitable recombinant DNA technique may be used in the production of the multichain polypeptides or proteins of the present invention. Typical expression vectors such as plasmids are constructed comprising DNA sequences coding for each of the chains of the polypeptide or protein.

It will be appreciated that a single vector may be constructed which contains the DNA sequences coding for more than one of the chains. For instance, the DNA sequences coding for Ig heavy and light chains may be inserted at different positions on the same plasmid.

Alternatively, the DNA sequence coding for each chain may be inserted individually into a plasmid, thus producing a number of constructed plasmids, each coding for a particular chain. Preferably the plasmids into which the sequences are inserted are compatible.

The or each constructed plasmid is used to transform a host cell so that each host cell contains DNA sequences coding for each of the chains in the polypeptide or protein.

Suitable expression vectors which may be use for cloning in bacterial systems include plasmids, such as Col E1, pcR1, pBR322, pACYC 184 and RP4, phage DNA or derivatives of any of these.

For use in cloning in yeast systems, suitable expression vectors include plasmids based on a 2 micron origin.

Any plasmid containing an appropriate mammalian gene promoter sequence may be used for cloning in mammalian systems. Such vectors include plasmids derived from, for instance, pBR322, bovine papilloma virus, retroviruses, DNA viruses and vaccinia viruses.

Suitable host cells which may be used for expression of the heterologous multichain polypeptide or protein include bacteria, such as $E.\ coli$ and $B.\ subtilis$, Streptomyces, yeasts, such as $S.\ cervisiae$, and eukaryotic cells, such as insect or mammalian cell lines. Examples of suitable bacterial host cells include $E.\ Coli$ HB 101, $E.\ Coli$ X1776, $E.\ Coli$ X2882, $E.\ Coli$ PS 410, $E.\ Coli$ MRC 1, $E.\ Coli$ RV308, $E.\ Coli$ E103S and $E.\ Coli$ B.

The present invention also includes constructed expression vectors and transformed host cells for use in producing the multichain polypeptides or proteins of the present invention.

After expression of the individual chains in the same host cell, they may be recovered to provide the complete multichain polypeptide or protein in active form, for instance to provide an Ig molecule of predetermined immunological function.

It is envisaged that in preferred forms of the invention, the individual chains will be processed by the host cell to form the complete polypeptide or protein which advantageously is secreted therefrom.

However, it may be that the individual chains may be produced in insoluble or membrane-bound form. It may therefore be necessary to solubilise the individual chains and allow the chains to refold in solution to form the active multichain polypeptide or protein. A suitable procedure for solubilising polypeptide chains expressed in insoluble or membrane-bound form is disclosed in our copending application No. (Protein Recovery, Agent's Ref. GF 402120 and 402121).

It will be appreciated that the present application shows for the first time that it is possible to transform a host cell so that it can express two or more separate polypeptides which may be assembled to form a complete multichain polypeptide or protein. There is no disclosure or suggestion of the present invention in the prior art, which relates solely to the production of a single chain heterologous polypeptide or protein from each host cell.

The present invention will now be described, by way of example only, with reference to the accompanying drawings, in which:

FIG. 1. shows a diagrammatic representation of a typical intact Ig molecule;

In the following examples, there is described the production of Ig light and heavy chain polypeptides derived from monoclonal antibodies which recognise and bind to the antigenic determinant 4-hydroxy-3-nitrophenyl acetyl (NP), using E. coli and S. cerevisiae as the host cells Recombinant DNA techniques were used to enable the host cells to express both the polypeptide chains.

It will be appreciated that the invention is not limited to the specific methods and construction described hereafter.

Construction of Lambda Light Chain Expression Plasmid

Figure 1:
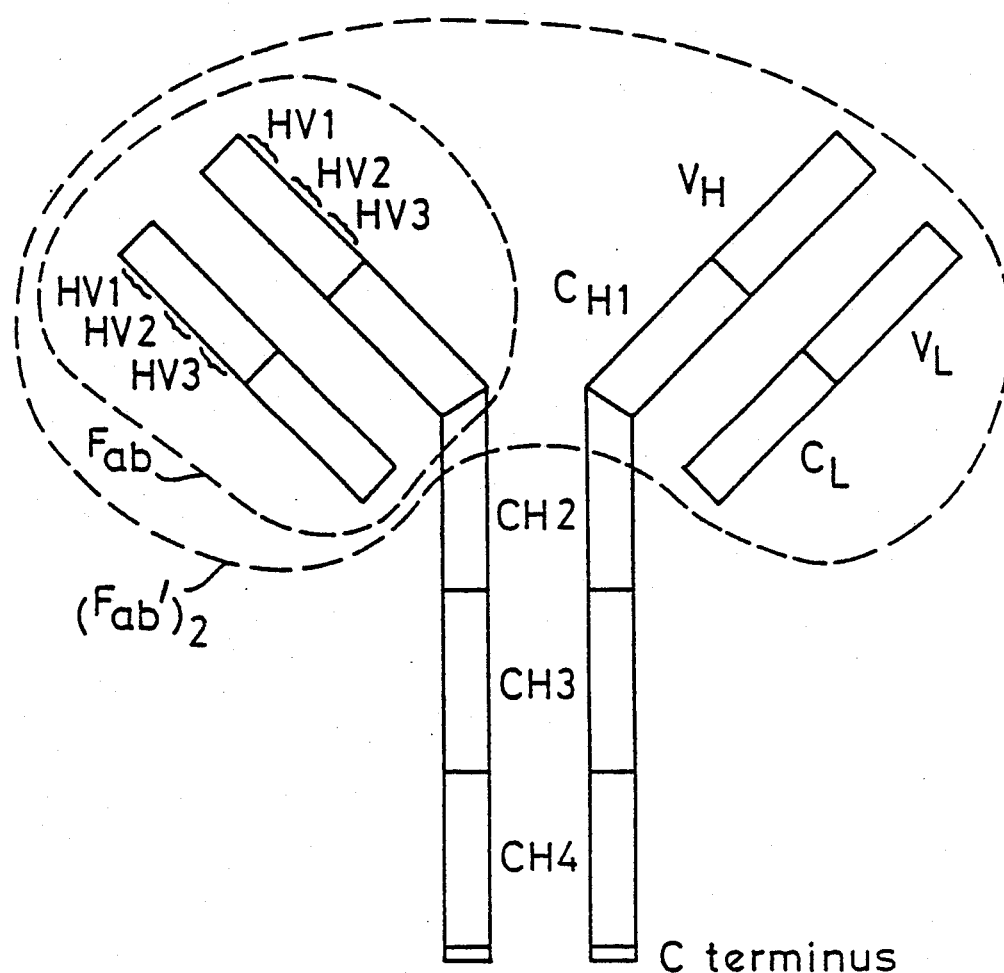
Figure 2:
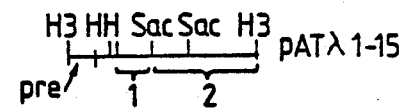
FIG. 2 shows the construction of plasmids for the direct synthesis of a $\lambda$ light chain in $E.\ Coli$.
Figure 2:
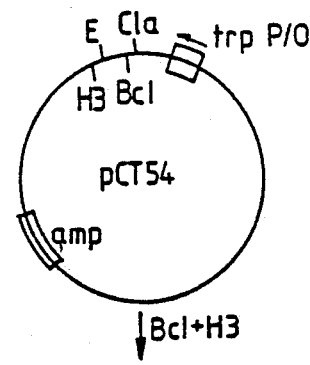

FIG. 2, to which reference is now made, shows schematically the method used to construct a λ light chain expression plasmid.

It was decided to express the lambda gene in E. coli by direct expression of the gene lacking the eucaryotic signal peptide but containing a methionine initiator residue at the amino-terminus (met-lambda). The approach used for bacterial synthesis of met-lambda was to reconstruct the gene in vitro from restriction fragments of a cDNA clone and to utilise synthetic DNA fragments for insertion into the bacterial plasmid pCT54 (Emtage et al., proc. Natl. Acad. Sci. USA., 80, 3671 to 3675, 1983). This vector contains the E. coli trp promoter, operator and leader ribosome binding site; in addition 14 nucleotides downstream of the ribosome binding site is an initiator ATG followed immediately by EcoR$_1$ and HindIII sites and the terminator for E. coli RNA polymerase from bacteriophage T7.

As a source of light chain we used a plasmid pABλ-1-15 which contains a full-length λ$_1$ light chain cDNA cloned into the PstI site of pBR322. This λ$_1$ light chain is derived from a monoclonal antibody, designated S43, which binds to 4-hydroxy-3-nitrophenylacetyl (NP) haptens.

In order to create a HindIII site 3' to the end of the lambda gene for insertion into the HindIII site of pCT54, the cDNA was excised from pAB λ 1-15 using PstI. The cohesive ends were blunt ended using the Klenow fragment of DNA polymerase and synthetic HindIII linker molecules of sequence 5'-CCAAGCTTGG-3' ligated. The DNA was digested with HindIII and the 850bp lambda gene isolated by gel electrophoresis and cloned into HindIII cut pAT153 to yield plasmid pAT λ 1-15. The 3' end of the lambda gene was isolated from pAT λ 1-15 by HindIII plus partial SacI digestion as a 630bp SacI-HindIII fragment (2 in FIG. 2). The HindIII cohesive end was dephosphorylated by calf intestinal alkaline phosphatase during isolation of the fragment to prevent unwanted ligations at this end in subsequent reactions.

A HinfI restriction site is located between codons 7 and 8 and the lambda sequence. The 5' end of the lambda gene was isolated as a 148bp HinfI to sacI fragment (1 in FIG. 2).

Two oligodeoxyribonucleotides were designed to restore condons 1-8, and to provide an initiator ATG as well as BclI and HinfI sticky ends. The two chemically synthesised oligonucleotides made to facilitate assembly of the gene had the sequences:

R45 5'-pGATCAATGCAGGCTGTTGTG 3'

R44 3' CCGACAACACTGAGTCCTTAp- 5' pCT54 was cut with both BclI and HindIII and the resulting linear molecules isolated, mixed together with the two oligodeoxyribonucleotide linkers R44 and R45 and both fragments 1 and 2, and ligated using T4 ligase (FIG. 2). The mixture was used to transform E. coli DH1 to ampicillin resistance. Recombinant clones in pCT54 were identified by hybridisation of DNA from replica plated colonies on nitrocellulose to a nick-translated probe derived from the pAT λ 1-15 insert.

A clone was identified which hybridised to lambda cDNA and also showed the predicted restriction fragment pattern. This plasmid (designated pCT54 19-1) was sequenced from the ClaI site and shown to have the anticipated sequence except that there was a mutation of the fourth codon from CTG to ATG, changing the amino acid at this point from valine the methionine.

The sequence in this area was:

```
... GATTGATCA.ATG.CAG.GCT.GTT.ATG.ACT.CAG.GAA.TCT.GCA.CTC.ACC.ACA.TCA
            met gln ala val met thr gln glu ser ala leu thr thr ser
```

The restriction enzyme sites in pCT54 between the Shine and Dalgarno sequence (AAGG), which is important for ribosome binding, and the ATG allow for the adjustment of the SD-ATG distance, an important parameter in determining expression rates. The SD-ATG distance was reduced by cutting the plasmid with ClaI or BclI and creating blunt ended species by digestion with S$_1$ nuclease. 2 μg of ClaI cut DNA was digested with 200 units of S$_1$ nuclease for 30 minutes at 30° using standard buffer conditions. The solution was deproteinised with phenol and the DNA recovered by ethanol precipitation. This DNA on religation with T4 DNA ligase and transformation into E. coli strain HB101 gave rise to a number of plasmids which had lost the ClaI or BclI site.

The plasmids which had lost their ClaI site were sequenced in the region surrounding the initiator ATG.

```
... AAGGGTATTGATCAATG CAG ... plasmid pNP3
    SD              met glu

... AAGGGTTTGATCAATG CAG      plasmid pNP4
    SD             met glu
```

In order to achieve high level expression a number of other approaches were followed. Firstly, a series of constructs were obtained which had increasing amounts of the 3' untranslated region of the cDNA removed by Bal 31 exonuclease. Secondly, a high copy number plasmid containing λcDNA was constructed. This plasmid contained a par function (Meacock, P. A. and Cohen, S. N., Cell, 20, 529-542, 1980) as well as being present in high copy number. Thirdly, the pNP3 plasmid was transformed into a number of protease-deficient strains or into HB101 in conjunction with a protease deficient dominant acting plasmid (Grossman, A. D. et al, Cell, 32, 151-159, 1983).

Construction of μ Heavy Chain Expression Plasmid

Figure 3:
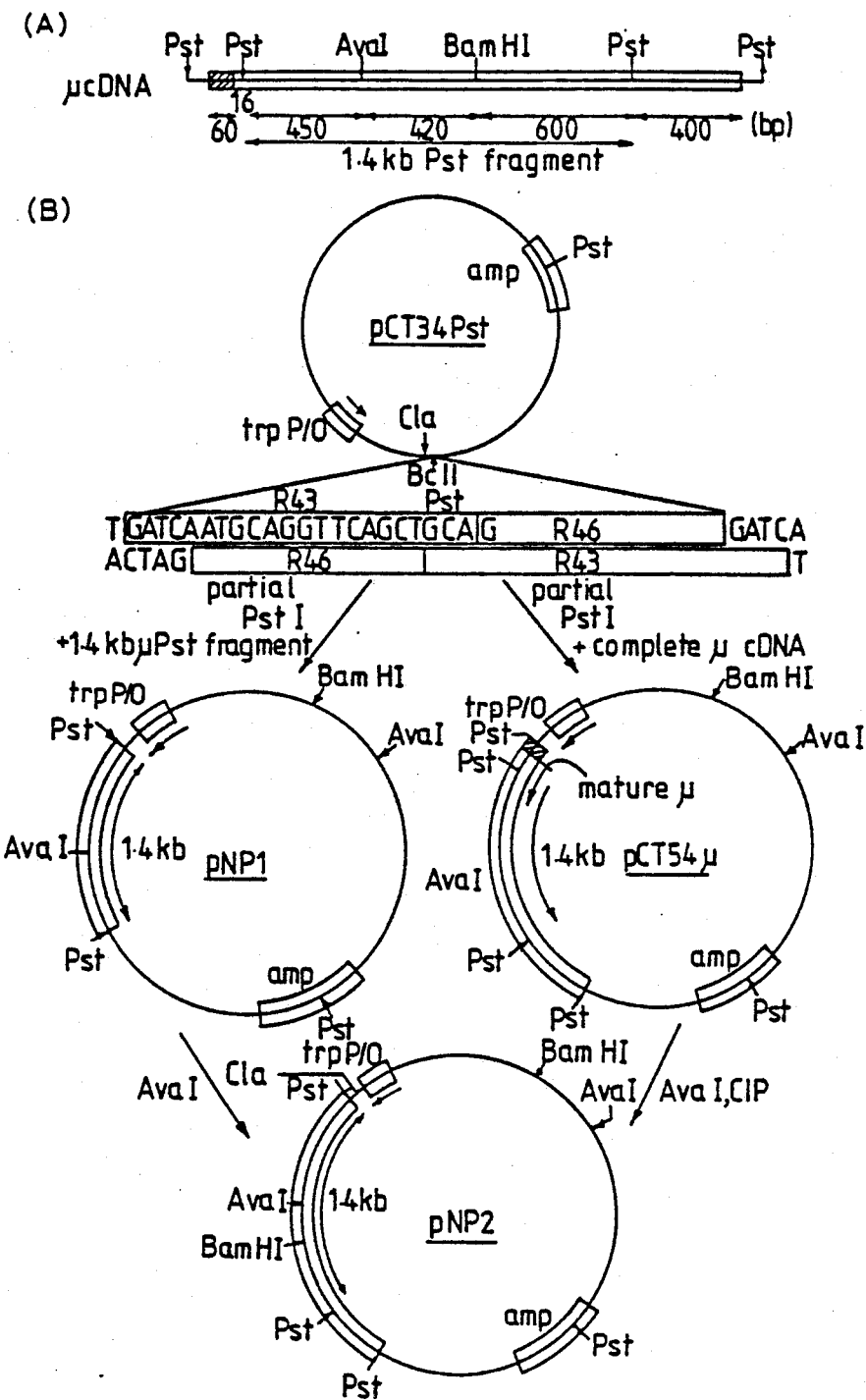
FIG. 3 shows the construction of plasmids for the direct synthesis of a $\mu$ heavy chain in $E.\ Coli$.

The full-length μ heavy chain cDNA derived from the NP binding monoclonal antibody B1-8 had been cloned into the PstI site of pBR322 yielding a plasmid designated pABμ-11 (Bothwell et al, Cell, 24, 625-637, 1981). In order to achieve high level expression, the μ cDNA minus the eukaryotic leader was reconstructed into pCT54. The construction of the μ heavy chain expression plasmid is shown diagramatically in FIG. 3. Two chemically synthesised oligonucleotides were made to facilitate this. These have the following sequences:

R43 5' GATCAATGCAGGTTCAGCTGCA 3'

R46 3' TTACGTCCAAGTCG 5'

These were ligated into BclI cut pCT54 using T4 DNA ligase and the resulting plasmid designated pCT54 Pst. The linkers were designed to replace the sequence in pCT54 between the BclI site and the ATG, to provide an internal PstI site and to recreate the sequence from pABμ-11 5' to the PstI site up to codon +1. pCT54 Pst was cut briefly with PstI, treated with alkaline phosphatase and full length DNA glass isolated from a 1% agarose gel. Similarly pABμ-11 was briefly cut with PstI and the full length μ insert isolated following agarose gel electrophoresis. The μ cDNA was ligated with the full length pCT54Pst fragment using T4 DNA ligase under standard conditions and a plasmid designated pCT54μ was identified which by restriction enzyme analysis was shown in contain a full-length μ insert. The plasmid was sequenced around the 5' linker region and was found to have the anticipated sequence:

5'...
TGATCAATGCAGGTTCAGCT-
GCAGGGGGGGGATGGATGGAG...3', demonstrating that it was, indeed, a full length clone. A complete PstI digest of pCT54μ liberated a 1.4 Kb fragment which was purified by 0.8% agrose gel electrophoresis and glass powder isolation. This was ligated with PstI cut pCT54 Pst (see above) using T4 DNA ligase under standard conditions, followed by transformation into HB101. A plasmid designated pNP1 was isolated which was shown by restriction endonuclease pattern analysis to contain the 1.4 Kb μcDNA fragment in an appropriate orientation (FIG. 3). pNP1 was a plasmid which consisted of an appropriate 5' end for expression, whilst pCT54 contained an appropriate 3' end. The full length gene was reconstructed into pCT54 by cutting both pNP1 and PCT54μ with AvaI which cuts once in the plasmid and once in the μ gene. Both digests were run on a 1% agrose gel and the 1.9 kb fragment from pNP1 and the 3.65 kb fragment from pCT54μ isolated. Following alkaline phosphatase treatment of the 3.65 pCT54μ fragment, the two pieces of DNA were ligated to each other and transformed into HB101. A plasmid designated pNP2 was identified which demonstrated the correct restriction endonuclease pattern. It was sequenced in the area surrounding the initiator ATG and found to have the anticipated sequence:

5'...
TTGATCAATGCAGGTTCAGCTGCAG-
CAGCCTGGGGCTGAGCTTGTGAAG...3'

The vector pCT54 had been constructed to include two restriction sites (Bcl1 and Cla1) between the S-D sequence (AAGG) and the initiation codon so that the distance between these sequence elements could be varied. As most E. coli mRNAs have 6-11 nucleotides between the S-D sequence and the AUG, the distance in pNP2 was reduced by modification at the Cla1 site. pNP2 was cut with Cla1 and incubated with S1. The amount of S1 nuclease was adjusted so that some DNA molecules would lose 1-2 extra base pairs as a result of 'nibbling' by the enzyme. This DNA on religation with T4 DNA ligase and transformation into E. coli strain HB101 gave rise to a number of colonies harbouring plasmids which had lost the Cla1 site. The sequences around the initiation codon of four plasmids pNP223, pNP261, pNP9 and pNP282 were determined and are given in Table 1, part A below.

TABLE 1

| | | S—D to ATG distance (no. of residues) | Sequence (5' - 3') Clot | Expression:(mu)(ru) expts. | | |
|---|---|---|---|---|---|---|
| | | | | A | B | C |
| (A) | pNP2 | 14 | —AAAAAGGGTATCGATTGATCA[ATG]CAGGTTCAG— | 0.7 | 0.6 | 0.8 |
| S1 derivatives of pNP2 | pNP223 | 12 | —AAAAAGGGTATATTGATCA[ATG]CAGGTTCAG— | — | 0.7 | 0.6 |
| | pNP261 | 10 | —AAAAAGGGTATTGATCA[ATG]CAGGTTCAG— | — | 1.1 | 1.1 |
| | pNP282 | 7 | —AAAAAGGGTGATCA[ATG]CAGGTTCAG— | — | 0.7 | 0.6 |
| | pNP9 | 9 | —AAAAAGGGTATGATCA[ATG]CAGGTTCAG— | 1.0 | 1.0 | 1.0 |
| (B) | pNP11 | 11 | —AAAAAGGGTATTGCACAT[ATG]CAAGTGCAA— | 5.3 | 6.3 | 9.1 |
| oligo constructs | pNP12 | 11 | —AAAAAGGGTATTGCACA[ATG]CAGGTTCAG— | 1.8 | 2.3 | 1.3 |

TABLE 1-continued

| | S—D to ATG distance (no. of residues) | Sequence (5' - 3') Clot | Expression:(mu)(ru) expts. | | |
|---|---|---|---|---|---|
| | | | A | B | C |
| pNP14 | 9 | —AAA<u>AAGGG</u>TATGATCA[ATG]CAAGTGCAA— | 72.2 | 106.7 | 124.6 |
| pNP8 | — | — | 77.0 | 53.4 | 145.5 |
| pCT70 | — | — | 0 | 0 | 0 |

The expression of these constructs in *E. coli* B was examined in three experiments, and concentrations of μ protein were determined by ELISA as relative units (ru), a measure of μ concentration normalised to pNP9. The results are shown in Table 1.

Inductions were carried out by resuspending cells at 1:50 dilution from overnight cultures into induction medium, consisting of: $KH_2PO_4$ (3 g/l), $Na_2HPO_4$ (6 g/l), NaCl (0.5 g/l), Difco vitamin assay casamino acids (30 g/l), $NH_4Cl$ (4 g/l), glycerol (16 g/l), proline (0.5 g/l), Difco yeast extract (1 g/l), $CaCl_2.6H_2O$ (0.022 g/l), $MgSO_4.7H_2O$ (0.025 g/l), thiamine (0.01 g/l) and carbenicillin (0.1 g/l). Cultures were shaken at 37° C. and cells harvested by centrifugation.

ELISA assays were performed essentially as described by Patel et al. (Nucleic Acid Research, 10, 5605 to 5620, 1982), using affinity purified goat anti-mouse IgM (Tago) and affinity purified goat anti-mouse IgM (Tago) conjugated peroxidase, with 3,3',5,5' tetramethylbenzidine (Miles) as a substrate. Bacterial cell pellets were boiled for 2 minutes in 9M urea (BRL) and loaded directly into the ELISA, such that all wells contained 2.25M urea, 10 mM Tris-HCl pH 7.8 150 mM NaCl, 0.05% NP40 and 0.5% casein (Hammarsten, B. D. H.).

Altering the S-D to ATG distance with nuclease S1 was found to increase the level of μ expression, relative, to the parental plasmid pNP2, but only to a small extent (compare pNP9). The optimal S-G to AUG distance was found to be 9–10 nucleotides, as found in pNP9 and pNP261 respectively.

Secondary Structure Analysis

Hairpin loops were identified by use of the computer programme HAIRGU developed by Dr. Roger Staden. The ΔG values were calculated as described by Trioco et al. (Nature NB, 246, 40–41, 1973).

Analysis of the potential secondary structure of μ mRNA encoded by pNP2 and pNP9 (one of the S1 derivatives of pNP2) revealed an extensive array of possible hairpin loops. Attention was focused on the region of this mRNA containing the ribosome binding site since the sequestering of S-D sequences and initiation codons into secondary structure may inhibit the initiation of translation. It was found that a hairpin loop including the U and G of the initiation codon could be formed (see FIG. 4). This hairpin loop is formed entirely within coding sequences and has a $\Delta G = -7.6$ kcal. No secondary structures were found which buried the S-D sequence, and none which mutually excluded the hairpin loop described above, and which had a lower ΔG.

To test whether expression of μ protein could be influenced by changes designed to alter potential secondary structure in the ribosome binding region, we used synthetic oligonucleotides to mutagenise this region of μ mRNA. The plasmids were constructed by insertion of a pair of oligonucleotides between the blunted Cla I site and the 5' Pst site of μ in pNP2 (see FIG. 5). The cloning strategy used to accomplish this, however, was multi-staged due to the presence of four Pst sites in pNP2. The vector pACYC184CM, which lacks Cla I and Pst I sites, was first constructed by cutting pACYC184 at its unique Cla I site, 'filling-in' the cohesive termini using T4 DNA polymerase and religating. Next, PACYC184CM was cut with BamHI, and the BamHI fragment from pNP2, bearing the 5'μ sequence, was inserted into it to form pCMμ (see FIG. 4). The vector pCMμ contained unique Cla I and Pst sites which were required for the oligonucleotide cloning (see FIG. 5).

pCMμ was cut with Cla I to completion, blunted with nuclease S1, and then cut with Pst I. The cut plasmid was purified by agarose gel electrophoresis and ligated separately with pairs of oligonucleotides, with the latter in a 100-fold molar excess. The pairs of oligonucleotides used were: R131 and R132 (for pNP11); R196 and R197 (for pNP12); and R202 and R203 (for pNP14). These have the sequences given below.

TGCACATATGCAAGTGCAACTGCA (R131),

GTTGCACTTGCATATGTGCA (R132),

GCTGAACCTGCATATGTGCA (R196),

TGCACATATGCAGGTTCAGCTGCA (R197),

GTTGCACTTGCATTGATC (R202),

GATCAATGCAAGTGCAACTGCA (R203).

The ligation mixture was then used to transform HB101. Recombinant clones were detected by colony hybridisation, on nitrocellulose filters, using one of each pair of oligonucleotides as a probe. Positive clones were sequenced and shown to have the correct nucleotide sequence. The μ sequences containing the cloned oligonucleotides were excised on Eco RV-Bgl II fragments. These were ligated to Eco RV-Bgl II cut pNP2 to reconstruct the full length μ genes (see FIG. 5). Three different plasmids were created by these procedures; pNP11, pNP12 and pNP14, having the nucleotide sequences shown in Table 1 above.

In the construct pNP11 the potentially deleterious hairpin loop of pNP2 was abolished by changing the residues in the degenerate position of three codons and by introducing a different S-D to AUG sequence. These changes allow the region between the S-D and AUG to base pair with the 5' end of μ coding sequence to form a hairpin loop of $\Delta G = -7.8$ kcal, approximately equal to that of pNP2, but leaving the AUG and S-D sequences exposed (see FIG. 4). The only other mutually exclusive hairpin loops are of $\Delta G = -2.3$, $-3.6$ and $+0.4$ kcal.

Figure 4:
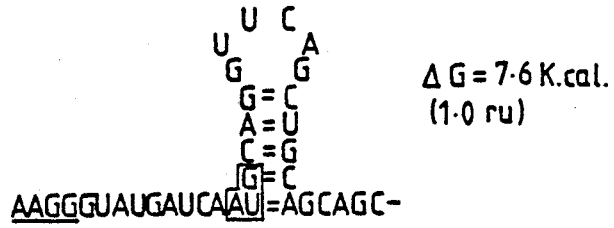
FIG. 4 is a diagrammatic representation of $\mu m$RNA sequences around the initiation codon.
Figure 4:
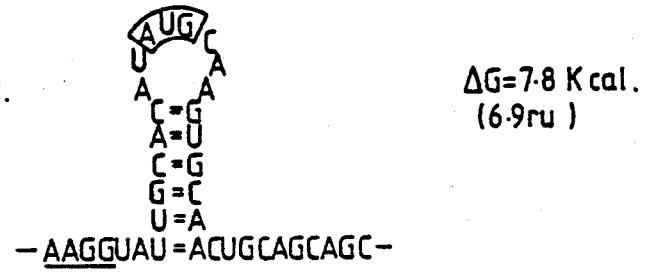
Figure 4:
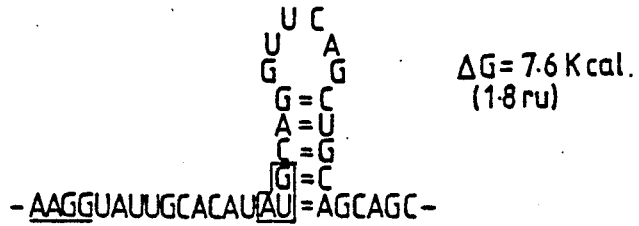
Figure 5:
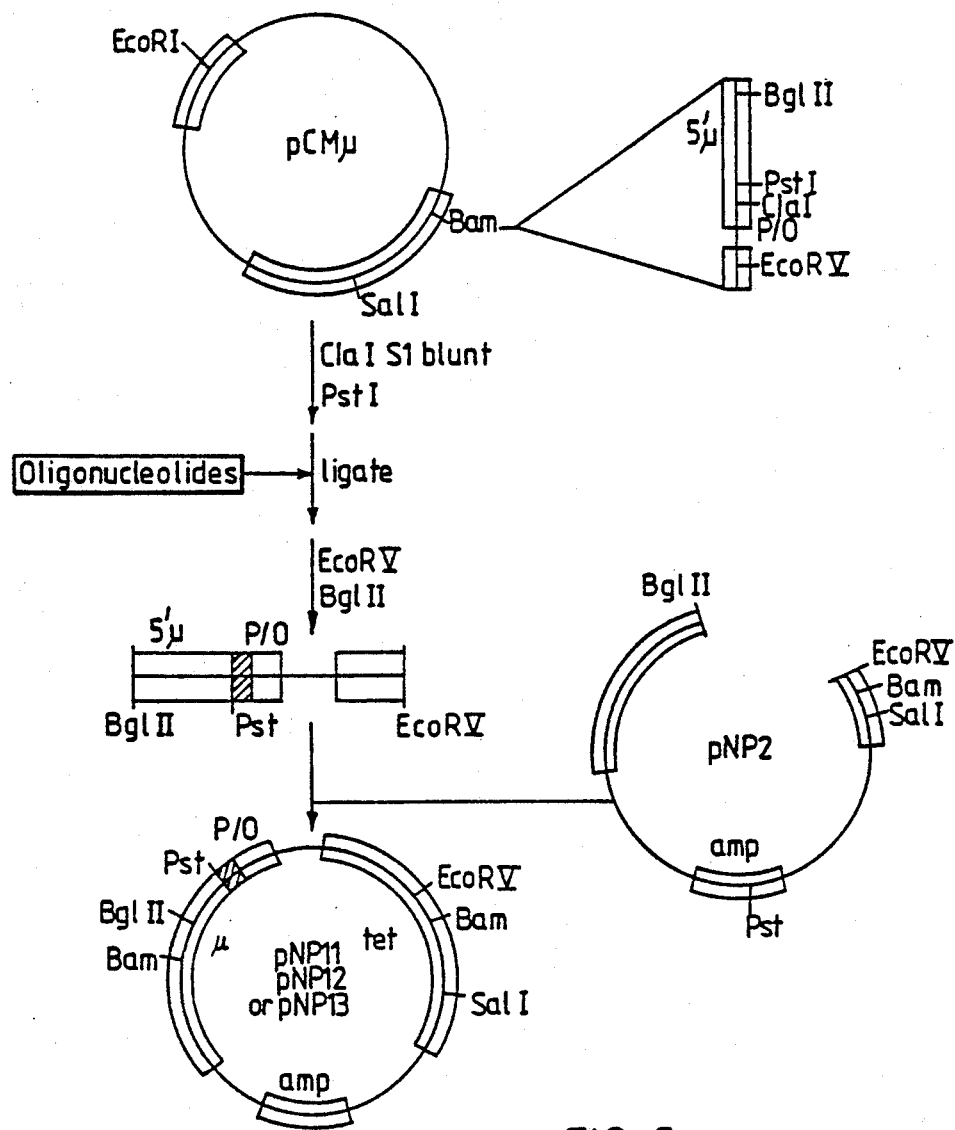
FIG. 5 shows the construction of plasmids having altered secondary structure around the initiation codon.

The construct pNP12 retains the S-D to AUG sequence of pNP11, but has the coding sequence of pNP2, such that the hairpin loop of pNP2 can form (see FIG. 4).

The final μ construct was pNP14, which had the S-D to AUG sequence of pNP9, but the 5' coding sequence of pNP11, so that the hairpin loop of pNP12 could not form. The construct pNB14 had no secondary structure burying the S-D or μ AUG.

μ Protein Expression from Constructs with Differing mRNA Secondary Structures E. coli B strains containing plasmids pNP9, pNP11, pNP12 and pNP14 were grown in induction medium and samples removed for ELISA assay. The concentration of μ was increased 6-7 fold in E. coli B cells containing pNP11 relative to pNP9 (see Table 1, Part b). Plasmid pNP12, which has the S-D to AUG sequence of pNP11, but the coding sequence of pNP9, showed only a two-fold increase in level of μ expression compared to pNP9.

Plasmid pNP14, which has the S-D to AUG sequence of pNP9 but the 5'μcoding sequence of pNP11, and thus differed from pNP9 only in three residues, was found to express μ protein over 90 times that found in pNP9.

A plasmid, pNP8, has also been constructed, from which μ is expressed, also from the trp promoter, as part of a trpE-μ fusion protein containing the amino terminal 53 amino acids of trpE and the carboxyl terminal 503 amino acids of μ. The rationale for making this fusion gene was that μ would be translated from an effective bacterial ribosome binding site rather than from one of unknown efficiency. Then, by comparing the amounts of trpE-μ produced from pNP8 with those of μ produced from the different constructs, an estimate of relative ribosome binding efficiency may be made. When the trpE-μ gene in pNP8 was induced and the products quantitated by ELISA, it was found that the μ expression in strains containing pNP8 and pNP14 was very similar (see Table 1, part B). The ribosome binding site (RBS) sequences of pNP11, pNP12 and pNP14 were designed in order to test the hypothesis that sequestering of the initiation codon into secondary structure inhibits translation initiation, and to increase the rate of initiation by releasing the initiation codon. In pNP11, the RBS hairpin loop of pNP2 and pNP9 was abolished by changing the 5'μcoding sequence in the degenerate position of three codons. In addition, the S-D to AUG sequence was changed to allow the base-pairing of this region with the 5' coding sequence. The result of these changes is that the initiation codon is exposed in the loop of a hairpin with the S-D sequence at the base of the stem (see FIG. 4). This hairpin loop had a ΔG approximately equivalent to the ΔG of the pNP9 hairpin loop. Strains containing pNP11 produced 6-7 times as much μ as did those with pNP9. To test whether this was due to the change in S-D to ATG sequence characteristics, rather than to the liberation of the initiation codon, pNP12 was constructed as a control. The latter has the S-D to AUG sequence of pNP11, but retains the 5'μ coding sequence of pNP9, so that the RBS hairpin loop of pNP11 cannot form, but the potentially deleterious one of pNP9 can form. The level of μ expression from pNP12 was found to be increased by only two-fold relative to pNP9. This increase is probably due to an altered S-D to AUG distance, a U immediately 5' to the initiation codon, and the S-D to AUG sequence being G-poor each of which has been shown to be advantageous. It is therefore likely that the increased expression from pNP11 is due to a preferable mRNA secondary structure. The RBS hairpin loop of pNP9 probably acts to inhibit translation while creation of another hairpin loop which exposes the initiation codon is responsible for the increased expression.

The plasmid pNP14 was constructed, such that it had the S-D to AUG sequence of pNP9, but the coding sequence of pNP11. The expression plasmid pNP14, therefore, differed from pNP9 in only three residues, those in the degenerate position of three codons, yet strains containing pNP14 expressed over ninety times more μ than those containing pNP9. This increase in expression cannot be explained on the basis of the three residue changes optimizing codon usage, for they introduce less favoured codons, as judged by the frequency of their occurrence in strongly expressed E. coli genes.

The increased expression is best explained by the abolition of the RBS hairpin loop in pNP9. The magnitude of the increases in expression observed, and the few residue changes introduced, makes it difficult for these results to be interpreted in terms of changes in mRNA stability.

The expression of pNP8, which encodes the trpE-μ fusion protein from a native trpE RBS, was also examined, and found to express at approximately the same level as pNP14. This may indicate that the RBS of pNP14 is equivalent to that of trpE in terms of its efficiency in directing translation initiation. The native trpE RBS of pNP8 and that of pNP14 were found to have no secondary structures hindering the use of their RBS sequences.

Expression of μ Protein in E. Coli

Figure 6:
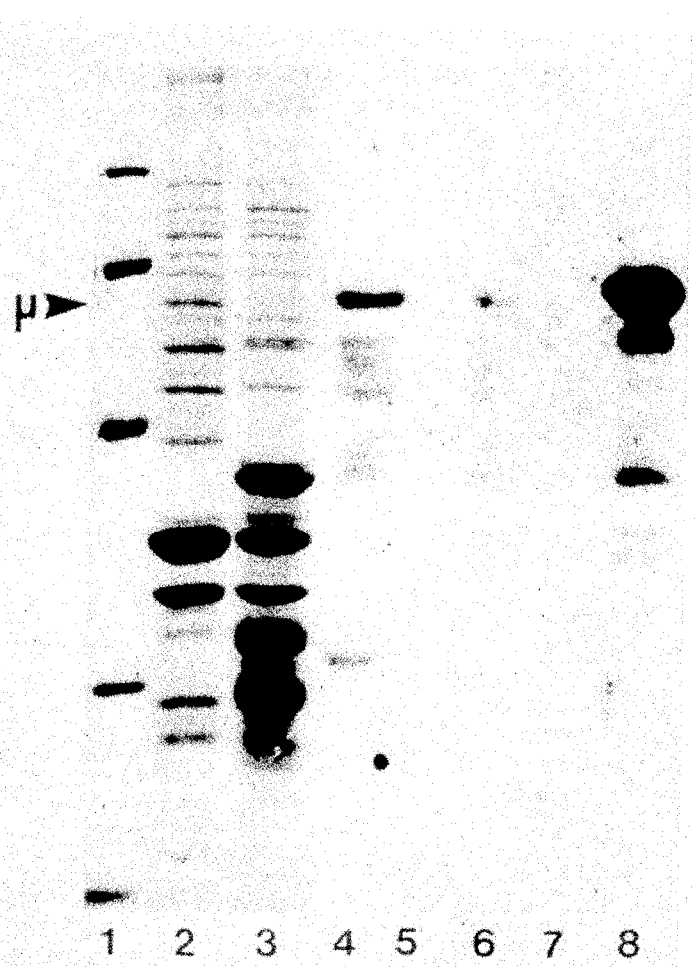
FIG. 6 is a polyacrylamide gel showing expression and distribution of $\mu$ protein from $E.\ Coli$ B.

E. Coli B cells containing the μ expression plasmid pNP11 were grown under inducing conditions and soluble and insoluble extracts prepared, and analysed by SDS-PAGE. A novel band was seen after staining the gel with Coomassie blue in the lane containing proteins from the insoluble fraction (see FIG. 6, lane 2). This band was not seen in the negative control lane which contained proteins from the same fraction from cells harbouring pCT70 (see FIG. 6, lane 3). The novel band was found to migrate to a position corresponding to a protein of a molecular weight within less than 5% of the actual molecular weight of non-glycosylated μ of 62.5 Kd. A duplicate set of lanes were transferred to nitrocellulose, and Western blotted. Alignment of the stained gel and the blot autoradiogram confirms that this novel band is antigenically related to IgM (see FIG. 6, lanes 4 and 8). No band was found in extracts from cells containing pCT70 (see FIG. 6, lanes 5 and 7). Only a low amount of μ was found in the soluble fraction (see FIG. 6, lane 6).

Figure 7:
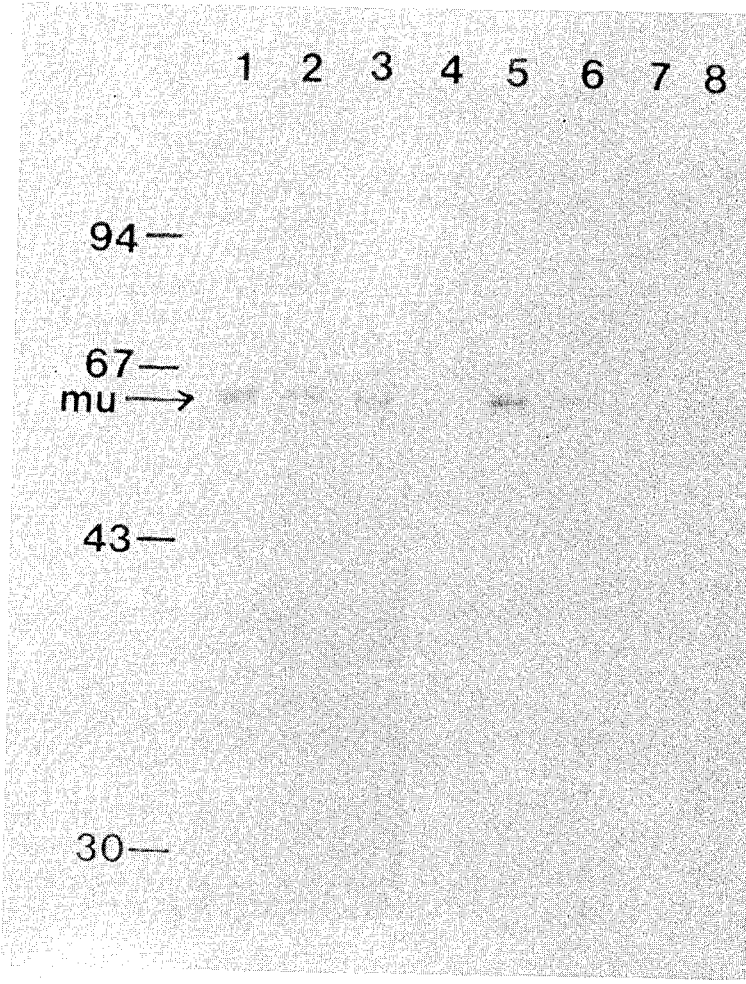
FIG. 7 is a polyacrylamide gel showing pulse chase autoradiograms of $\mu$ protein in $E.\ Coli$ B and in $E.\ Coli$ HB101.

A greatly increased level of expression of μ was found in E. Coli B compared to HB101. Pulse chase analysis demonstrated that in E. Coli B, a similar level of μ protein was detected after a 60 minute chase (FIG. 7, lane 3) as was seen after the initial labelling period (FIG. 7, lane 1). In HB101, however, very little μ protein could be seen after a 10 minute chase (FIG. 7, lane 7), and none after 30 minutes (FIG. 7, lane 8), compared to the amount detected after the initial labelling period (FIG. 7, lane 5).

For pulse chase analysis, inductions were set up as described above, except that the medium used consisted of: proline (0.3 g/L), leucine (0.1 g/L), Difco methionine assay medium (5 g/L), glucose (60 mg/L), thiamine (10 mg/L), CaCl$_2$ (22 mg/L), MgSO$_4$ (0.25 g/L)m and carbenicillin (0.1 g/L). During exponential growth cells were pulse labelled with 30 μCi/ml L-[$^{35}$S]methionine for 2 minutes, after which unlabelled methione (100 μg/ml) was added and the incubation continued for the times indicated.

Induced *E. Coli* B cells harbouring pNP14 when examined by phase contrast microscopy were found to contain inclusion bodies.

Expression of λ Light Chain in *E. Coli*

A fresh 1 ml overnight culture of *E. Coli* HB101 or RV308 containing the plasmid under study was grown in L Broth (Maniatis et al,, Molecular Cloning, Cold Spring Harbor Laboratory, 1982), supplemented with carbenicillin to 100 μg/ml.

A 1:100 dilution of this culture was made into M9 medium (Maniatis, 1982, op.cit.) supplemented with glucose, vitamin B$_1$, carbenicillin, leucine and proline and the cultures shaken at 37° for 5-6 hours. At this time $^{35}$S-methionine was added for 5-20 minutes. The cells were then harvested by centrifugation, lysed by boiling in 1% SDS for 2 minutes and diluted by addition of a buffer consisting of 2% Triton X-100, 50mM Tris pH 8, 0.15M NaCl and 0.1 mM EDTA. Immunoprecipitations were carried out by addition of antisera to aliquots of labelled *E. Coli* extracts and, after incubation at 4° overnight, immune complexes were isolated by binding to Staphylococcus aureus fixed cells. The complexes were dissociated by boiling in 60 mM Tris pH 6.8 buffer containing 10% glycerol, 3% SDS and 5% mercaptoethanol and the liberated proteins analysed on 10% or 12.5% acrylamide/SDS gels (Laemmli, UK. Nature, 227, 680–685, 1970). Gels were stained with Coomassie Brilliant blue to visualise the protein bands while labelled proteins were detected on Fuji-RX film by fluorography using 1M sodium salicylate.

Figure 8:
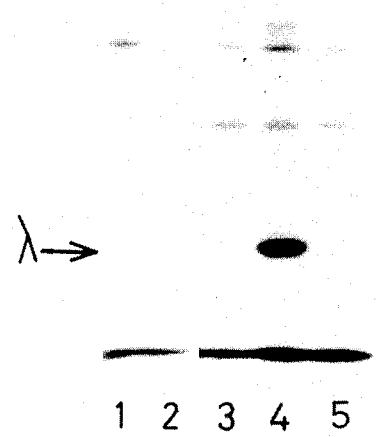
FIG. 8 is a polyacrylamide gel showing the results of $\lambda$ gene expression in $E.\ Coli$.

HB101 cells containing pNP3 and other plasmids were grown under inducing conditions to an OD$_{600}$=0.6 and the proteins present examined by specific immunoprecipitation substantially as described above. The results obtained are given in FIG. 8, in which lanes 1 and 2 respectively were extracts from pCT54-19 and pNP3, immunoprecipitated with normal rabbit serum; lanes 3, 4 and 5 were extracts immunoprecipitated with rabbit anti-lambda serum and represent pNP4 (lane 3), pNP3 (lane 4) and pCT54-19 (lane 5). The position of unlabelled lambda protein from MOPC104E is indicated on the left hand side of FIG. 8. All of the plasmids produced a protein which reacted with rabbit anti-mouse λ light chain serum and comigrated with authentic λ$_1$ light chain from the mouse myeloma MOPC104E. pNP3 however produced the most of this protein (compare lane 4 with lanes 3 and 5 in FIG. 8). No such band was detected with control immunoprecipitations using normal rabbit serum (FIG. 8, lanes 1 and 2). Studies using brief pulses with $^{35}$S-methionine followed by chasing with excess cold methionine indicated that the recombinant λ light chain had a ½ life of about 20 minutes.

In vitro transcription/translation (Pratt et al, Nucleic Acids Research, 9, 4459–447, 1981) confirmed that pNP3 coded for a protein which comigrated with authentic λ light chain. This 25 Kd product was synthesized in vitro at a rate comparable to that of β-lactamase indicating that it is synthesised in vivo at a level of 0.5% of total *E. Coli* proteins. This figure is in good agreement with the percentage of recombinant λ product synthesised in vivo (0.4–2%) as determined from the following equation:

% specific CPM =

$$\frac{100 \times (CPM \text{ with anti-}\lambda) - (CPM \text{ with normal serum})}{total\ CPM}$$

The procedure used to disrupt cells was as follows (Emtage J S et al, Proc. Natl. Acad. Sci., 80, 3671–3715, 1983). *E. Coli* HB101/pNP3 grown under inducing conditions were harvested and resuspended in 0.05M Tris pH 8, 0.233M NaCl, 5% glycerol containing 130 g/ml of lysozyme and incubated at 4° C. or room temperature for 20 minutes. Sodium deoxycholate was then added to a final concentration of 0.05% and 10 μg of DNAase 1 (from bovine pancreas) was added per g wet wt of *E. Coli*. The solution was incubated at 15° C. for 30 minutes by which time the viscosity of the solution had decreased markedly. The extract was centrifuged (at 10,000×g for 15 minutes for small volumes (1 ml) or 1 hour for larger volumes) to produce a soluble and an insoluble fraction.

Figure 9:
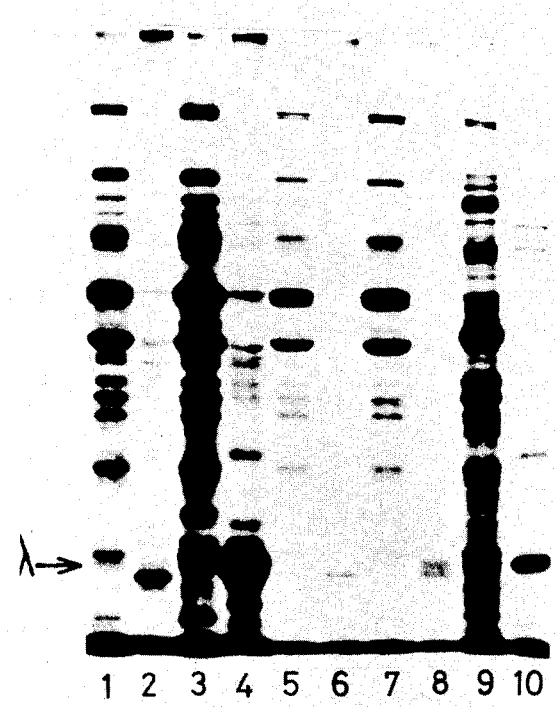
FIG. 9 is a polyacrylamide gel showing the distribution of recombinant $\lambda$ light chain polypeptide between the soluble and insoluble cell fractions.

For immunoprecipitations, the soluble fraction was diluted in the Triton-containing buffer described above and the insoluble fraction solubilised by boiling in 1% SDS followed by dilution in Triton-containing buffer. HB101 cells containing pNP3 or pNP4 were grown under inducing conditions, pulse labelled with [$^{35}$S]methionine, separated into soluble and insoluble fractions and analysed by sodium dodecyl sulfate polyacrylamide gel electrophoresis. The results obtained are shown in FIG. 9 in which lanes 1 and 3 correspond to the soluble fraction from HB101-pNP3 immunoprecipitated with normal rabbit serum and rabbit anti-lambda serum respectively; lanes 2 and 4 correspond to the insoluble fraction from HB101-pNP3 immunoprecipitated with normal rabbit serum and rabbit anti-lambda serum respectively, lanes 5 and 7 correspond to the soluble fraction from HB101-pNP4 immunoprecipitated with normal rabbit serum and rabbit anti-lambda serum respectively; lane 9 corresponds to the soluble fraction from HB101-pNP3, and lane 10 corresponds to the insoluble fraction from HB101-pNP3. The position of unlabelled lambda protein from MOPC104E is indicated on the left hand side of FIG. 9. When such a procedure was carried out using pNP3, the recombinant λ light chain protein was present in the insoluble fraction (FIG. 9, lane 4) rather than the soluble fraction (FIG. 9, lane 3). No 25 Kd band comigrating with authentic λ$_1$ light chain was present when either the soluble or insoluble fraction were immunoprecipitated using normal rabbit serum (FIG. 9, lanes 1 and 2). By inference it is likely that all Ig light chains will fractionate as in this specific example.

Figure 10:
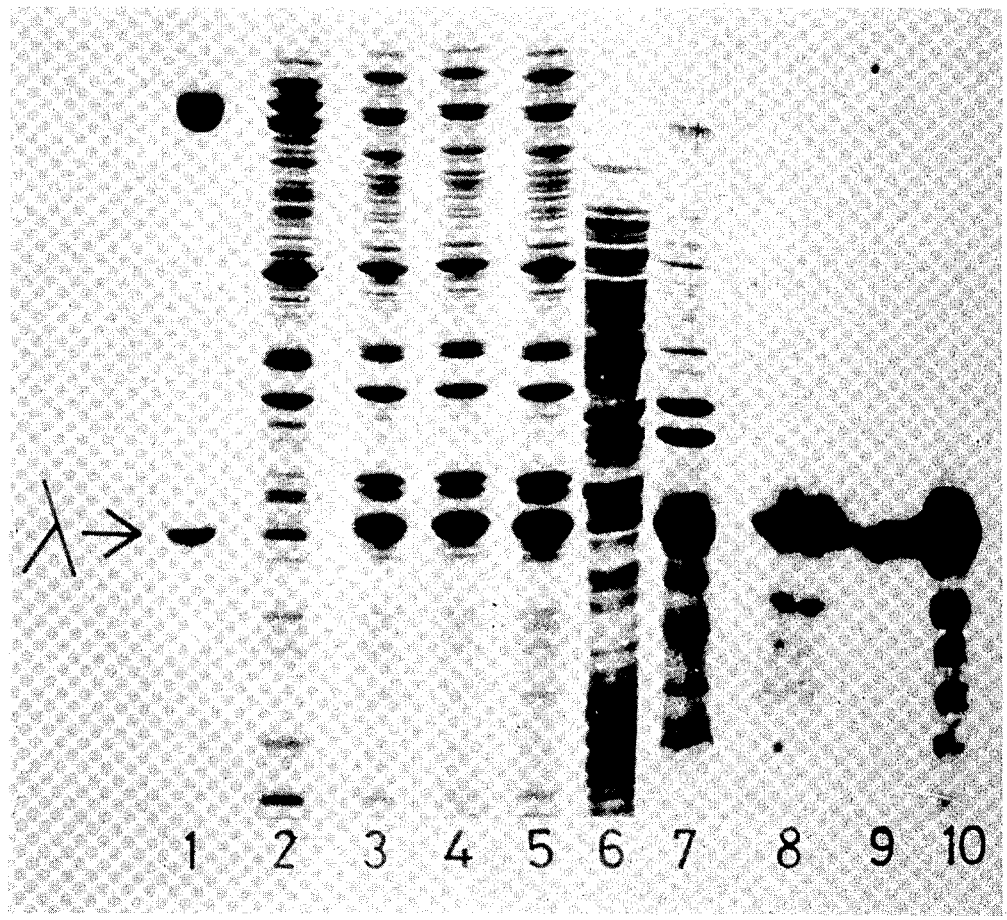
FIG. 10 is a polyacrylamide gel showing expression and distribution of $\lambda$ protein from $E.\ Coli$ E103S.

In the absence of specific immunoprecipitation a novel protein band was not visible from extracts of HB101 containing pNP3 nor was the λ protein found to accumulate. However, there was a dramatic difference when pNP3 was induced in the K12 strain E103s. In this strain λ protein was found to accumulate during induction until the cells reaches stationary phase (FIG. 10, lanes 3–5) to a level of about 150 times that found in HB101 as determined by an ELISA (enzyme linked immunosorbent assay). These cells were found to contain inclusion bodies which appeared refractile under light microscopy, a phenomenon characteristic of high level expression of foreign proteins. An estimate of the pecentage of total E. coli protein represented by recombinant λ protein was obtained by separating the proteins by gel electrophoresis, staining them, with Coomassie blue and scanning the stained gel with a Joyce-Loebl chromoscan 3. This method showed that λ was the major protein present (FIG. 10, lane 5) and represented 13% or total E. coli protein. The λ protein had a half-life of 20 minute in HB101 but accumulated to very high levels in E103s, suggesting that lambda protein was much more stable in the latter strain. After cell lysis and centrifugation of HB101 or E103s containing pNP3, λ light chain was detected in the insoluble (FIG. 10, lanes 7 and 10) but not in the soluble fractions (FIG. 10, lanes 6), as determined by Coomassie blue staining. The identity of the major Coomassie blue stained band as λ protein was confirmed by Western blot analysis (FIG. 10, lanes 8-10). The presence of such immunoreactive bands was specific to pNP3 containing cells. When extracts from cells containing pCT70, a prochymosin expressing plasmid, were subjected to the same analysis no bands were detected. This more sensitive technique showed that a small amount of the λ protein was in the soluble fraction (FIG. 10, lane 9). The presence of a number of distinct immunoreactive proteins all smaller than full-length protein were also detected. These may result from proteolytic degradation of of λ protein, from premature termination of transcription or from internal initiation of translation.

Expression of μ and Lambda Polypeptides in the same Bacterial Cell

Each of the Ig μ and λ genes in expression plasmids were transformed into the same E. Coli cell to direct the synthesis of both Ig μ and λ polypeptides. In order to overcome plasmid incompatibility and provide a second antibiotic resistance marker, the trp promoter and λ sequences were excised from pNP3 on a Hind III-Bam HI fragment and inserted into the Hind III-Bam HI fragment of pACYC 184. The resultant plasmid pACYC λ caused the E. coli to grow very poorly. This weak growth was thought to result from read-through of RNA polymerase into the origin of replication. However, the inhibition of growth was virtually eliminated by the cloning in of the baceteriophage T7 transcriptional terminator at the Hind III site of plasmid pACYC λ.

This terminator functions in both orientations. The resultant plasmid pAC λ T7-1 has a chloroamphenicol resistance gene and an origin compatible with the pBR 322-derived origin on pNP14, the Ig μ expressing plasmid. Transformation of both plasmids in the same E. Coli B was achieved in two steps. Firstly pNP14 was introduced followed by pAC λ T7- I in two sequential transformations to give ampicillin and chloramphenicol resistant clones.

E. Coli B cells derived form this double-transformant clone showed the presence of inclusion bodies and two novel polypeptide bands on stained gels of the insoluble fraction after lysis. These two bands correspond both with immunological activity by Western blotting for Ig μ and Ig λ and in their expected molecular weights. It has thus been shown that the double-transformant clone expresses both the heterologous genes. This had not hitherto been shown.

The presence of λ light chain in the insoluble fraction was a useful purification step since it both concentrated the protein and separated if from the bulk of E. Coli soluble proteins.

For further purification of the λ light chain, the cell debris were dissolved in 10 mM Tris-HCl pH8.0, 25% formamide, 7M urea, 1 mM EDTA and 2 mM dithiothreitol. This material was loaded onto a DEAE Sephacel column (Pharmacia) (1×25 cm at a flow rate of 5 ml/hr) which had been equilibrated in 9M urea, 10 mM Tris-HCl pH 8.0, 1 mM EDTA and 2 mM DTT. The DEAE Sephacel column was developed using a 0-150 mM NaCl gradient in loading buffer. The eluted peak λ light chain immunoreactivity, corresponding to the major peak of protein, was diluted to a final concentration of 2.25M urea, 10 mM Tris-Hcl pH 8.0, 1 mM EDTA, 2 mM DTT and loaded onto an octylSepharose column (Pharmacia) (2.5×10 cm). Material was eluted by use of a urea gradient of 2.25-9M urea. The peak material was pooled, dialysed into ammonium bicarbonate and lyophilised. Following this step, only a single band of Coomassie blue stainable material corresponding to recombinant λ protein was visualised by SDS-PAGE.

The μ heavy chain was purified from 9M urea solubilised pellets by anion exchange chromatogrpahy and chromatofocussing (Pharmacia).

It was of great interest to determine whether the concomitant expression of μ and λ would lead to the formation of functional IgM. In order to determine this, extracts were made from E. coli containing both Ig μ and λ polypeptides and these tested for antigen binding. We used a two-site sandwich ELISA which detects μ chain binding to haptenalated bovine serum albumin (NIP-caproate-BSA).

In the NIP binding assay, bovine serum albumin (BSA) is reacted with an equimolar amount of NIP-Cap-N-hydroxy-succinamide at pH 7.5 in 10 mM phosphate buffer. The resulting NIP-Cap-BSA is separated from free NIP-Cap on a G-50 Sephadex column.

Microtitre plates (96 well Nunc Immuno Plate 1) are coated with 100 μl of a solution of 10 μg/ml NIP-BSA in sodium carbonate/sodium bicarbonate 0.1M, pH 9.6 buffer (coating buffer) overnight at 4° C.

The coated plates are then blocked for non-specific binding by addition of 100 μl of 0.5% casein in coating buffer (blocking buffer) and incubating at 37° C. for 1 hour.

The coated and blocked plates are then washed three times in 150 mM NaCl, 0.05% NP40, 20 mM Tris-HCl, pH 7.8 buffer (washing buffer).

The washed plates are shaken free of excess washing buffer and samples are added in their buffer or typically in 0.5% casein in washing buffer (sample buffer) to a 100 μl final volume.

In order to demonstrate the nature of the binding to NIP-BSA, samples for testing were supplemented with either NIP or NP is free solution at various concentrations (from 60 to 0.3 μM for NIP or from 600 to 3 μM for NP).

The plates with samples are then incubated at 37° C. for one hour and thereafter washed three times with washing buffer.

The washed plates are then innoculated with 100 μl of anti μ-peroxidase conjugate (1:1000 dilution; TAGO Inc) in sample buffer, and incubated for one hour at 37° C. The plates are then washed three times in washing buffer.

The washed plates are innoculated with 100 μl of 0.1M Na acetate-citrate, pH 6.0, 0.1 mg/ml tetramethylbenzidine, 13 mM $H_2O_2$ (peroxidase substrate) and incubated at room temperature for one hour. The reaction is terminated by the addition of 25 μl of 2.5M $H_2SO_4$.

The microtitre plates are then read in a plate reader (Dynatech) at 450 λm with a reference of 630 λm. The $A450$ was related to the level of a standard protein, Bl-8 anti-NIP IgM.

This assay demonstrates sensitivity to 60 pg of Bl-8 IgM. The extracts were prepared as soluble and insoluble material. The insoluble material was solubilized in the same buffer used in lysis but containing 8M urea followed by its dilution for assay.

In order to obtain activity for the Ig μ and λ, extracts were made of the insoluble fraction and these dialysed into buffer conditions in which disulphide interchange will occur at a higher frequency.

Production of functional antibodies from E. Coli expressing both heavy and light chains was achieved by lysing the cells and clarifying the supernatant by centrifugation. The insoluble material was washed, followed by sonication (3 times for 3 minutes), and finally dissolved in 9M urea, 50 mM glycine-NaOH pH 10.8, 1 mM EDTA, and 20 mM 2-mercaptoethanol. This extract was dialysed for 40 hours against 3 changes of 20 vols. of 100 mM KCl, 50 mM glycine-NaOH pH 10.8, 5% glycerol, 0.05 mM EDTA, 0.5 mM reduced glutathione and 0.1 mM oxidised glutathione. The dialysate was cleared by centrifugation at 30,000 g for 15 minutes and loaded directly onto DEAE Sephacel, followed by development with a 0-0.5M KCl linear gradient in 10 mM Tris-HCl, 0.5 mM EDTA, pH 8.0.

The purified Ig μ and λ were treated as above, except that no anion exchange chromatography was carried out. The preparation was finally dialysed into phosphate buffered saline, 5% glycerol, 0.01% sodium azide and 0.5 mM EDTA pH 7.4.

Figure 11:
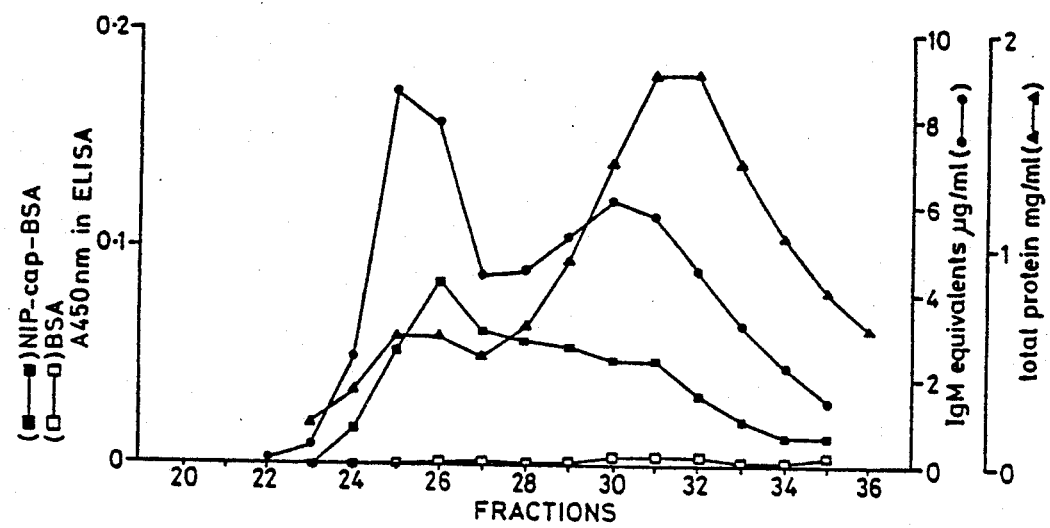
FIG. 11 shows the results of the fracitonation of $\mu$ and $\lambda$ protein expressed by $E.\ Coli$ B on DEAE Sephacel.

The results from assays of material processed in this way indicated that some activity was obtained. The level of activity obtained in this way was too low to do any detailed studies on, so the resultant dialysate was purified by anion exchange chromatography (FIG. 11). This process resulted in the isolation of significant NIP-cap-BSA binding activity over that of background binding to BSA (FIG. 11). The assay of the fractions for the level of Ig μ, expressed as Bl-8 IgM equivalents demonstrated two peaks of activity. This was not found to correlate with full length Ig μ by Western blotting. The first peak observed may represent a fragment of Ig μ. The separation of NIP-CAP-BSA binding activity from the majority of full length Ig μ and protein indicates that the hapten binding activity is contained within a particular molecular species formed at low efficiency.

The processing of insoluble material obtained from Ig μ expression in E. Coli produced a similar IgM protein profile but without NIP-cap-BSA binding activity. This demonstrates that the activity recovered was a property of the combined immunoglobulin expression, not of some E. Coli factor, or of the Ig μ heavy chain alone.

Figure 12:
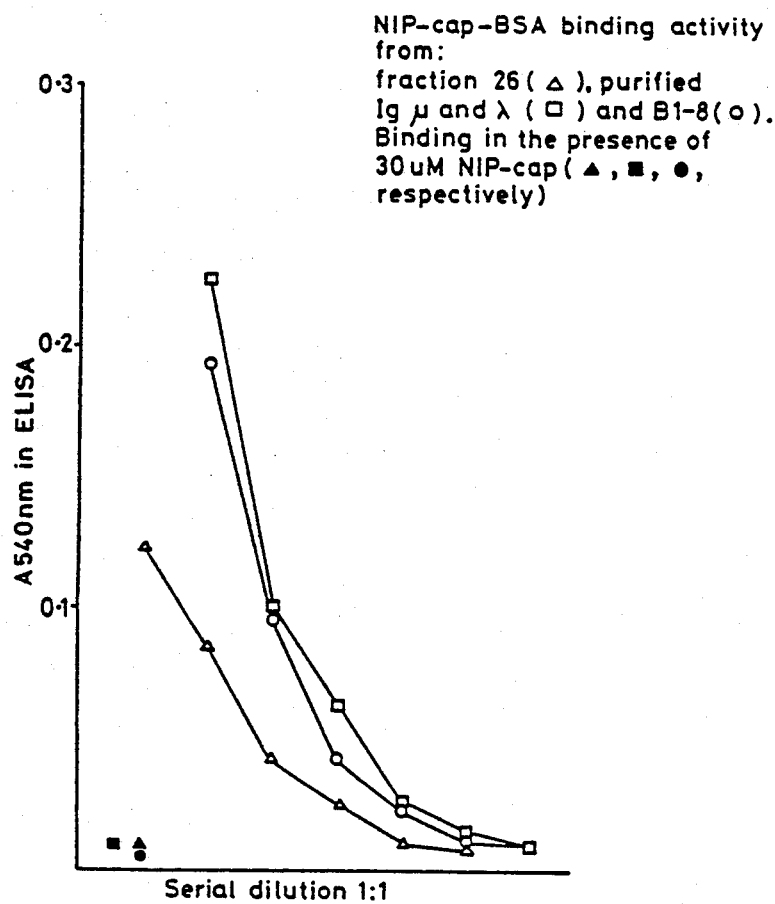
FIG. 12 shows the specific hapten binding of reconstituted Ig molecules.

Further studies of the characteristics of the hapten (NIP-cap-BSA) binding were carried out. As samples were diluted they showed less binding to hapten in a very similar way to the original antibody (FIG. 12). Free hapten was found to inhibit most of the binding activity in both indiluted and diluted samples. Using Bl-8 antibody as a standard for both IgM and hapten binding, the specific activity of the assembled antibody was calculated to be $1.4 \times 10^4$ gm/gm of IgM equivalents. This value demonstrates the inefficient recovery of activity, but possibly represents an underestimate of the specific activity due to an overestimate of full-length Ig μ in these fractions, as described above.

Heteroclitic Nature of Recombined Antibody

Figure 13:
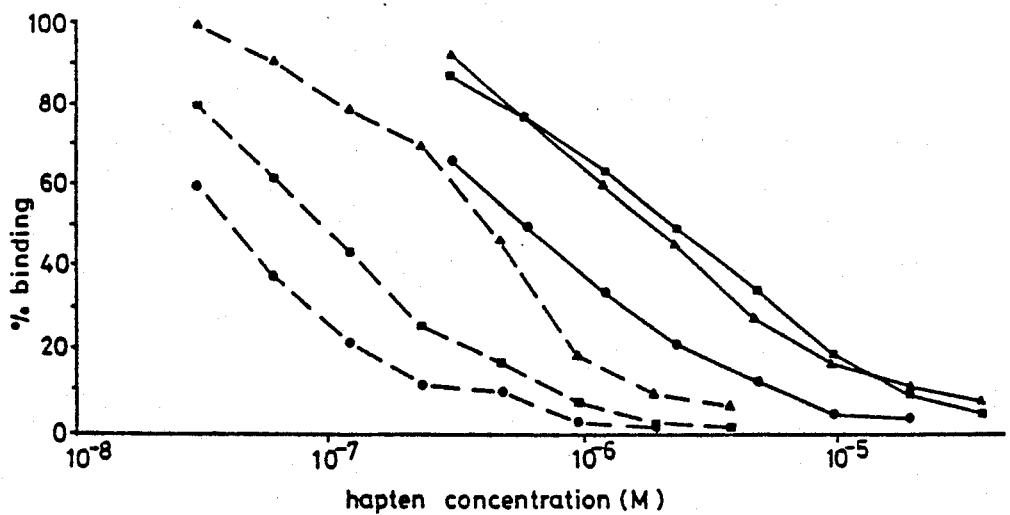
FIG. 13 shows the heteroclitic nature of the hapten binding of the reconstituted Ig molecules.

Detailed specificity of binding to NIP-cap-BSA was investigated by comparing the assembled antibodies with Bl-8 IgM in the presence of free NIP-cap and NP-cap (FIG. 13). Both Bl-8 IgM and the assembled antibodies showed that higher NP-cap than NIP-cap concentrations were required to inhibit NIP-cap-BSA binding.

The heteroclitic nature is demonstrated by the molar ratio of NIP to NP at 50% inhibition. The concentrations of NIP and NP at 50% inhibition (I50) were found to be similar for both Bl-8 and the assembled antibodies as shown in Table 2. Also the NP I50/NIP I50 ratios were similar (Table 2).

TABLE 2

| Hapten concentration at 50% inhibition (I50) of binding of antibodies to NIP-cap-BSA solid phase. SD = Deviation. | | | |
|---|---|---|---|
| | NIP I50 uM | NP I50 uM | NP I50/NIP I50 |
| Bl-8 IgM | 0.13 (SD, 0.05) | 3.7 (SD, 2.9) | 29 |
| Fraction 26 | 0.24 (SD, 0.09) | 1.9 (SD, 0.4) | 6 |
| Fraction 27 and 28 | 0.11 (SD, 0.02) | 1.1 (SD, 0.3) | 10 |
| Purified μ and λ | 0.4 | 0.84 | 22 |

It has thus been shown that not only is it possible to express μ and λ proteins having intact variable domains, but also that it is possible to express both μ and λ proteins on compatible plasmids in the same cell. This latter has not hitherto been disclosed or even suggested. Moreover, it proved possible to derive functional Ig molecules from E. Coli cells which expressed both μ and λ proteins.

It has thus been shown that the process of the present invention produces a functional Ig molecule by recombinant DNA techniques.

Construction of Expression Plasmids for Yeast

The plasmids used for expression in yeast (Saccharomyces cerevisiae) are based on pBR322 and the yeast 2 micron plasmid. These plasmids are the subject of co-pending European Patent Application EP 0 073 635, the disclosure of which is incorporated hereby reference. The yeast phosphoglycerate kinase gene (PGK) provides the 5′ sequence necessary for initiation of transcription and insertion of genes can be made at the unique BglII site in the plasmid pMA 3013 described in the above mentioned European patent application. This plasmid has now been renamed pMA91 as is so referred to hereinafter.

(a) met-mu (μ)

BglII and BclI produce compatible 5′-GATC ends. The met-μ gene from pNP2 was excised on a partial BclI fragment and ligated into the unique BglII site of pMA91.

(b) Pre-mu (μ)

The plasmid pCT54 u containing the full lengths pre-μ cDNA was digested with Hind III. This cuts at the 3′ side of the μ cDNA. This Hind III site was changed to a BclI site by incubation with T4 DNA polymerase in the presence of all 4 nucleotides. The linker R107 of sequence TTTTGATCAAAA, which contains an internal BclI was ligated to the DNA obtained above. After ligation one aliquot of the resultant DFNA was digested with BcII and AccI and the μ AccI-BcII fragment was isolated from the resultant mixture by gel electrophoresis. A separate aliquot of the resultant DNA was digested with MboII and ligated with chemically synthesised oligonucleotide linkers R121 and R112 which have cohesive BcII and MboII ends.

R121 5' GATCAATGGGATGGAGCTGT 3'

R112 5' TTACCCTACCTCGAC 3'

The ligation reaction was terminated and the resultant DNA digested with AccI to give a μ MboII-AccI fragment which was isolated from the resultant mixture by gel electrophoresis on a 5% polyacrylamide gel.

The two μ fragments obtained above were ligated together and then digested with BcII to eliminate unwanted ligation products after which the resultant pre-μ DNA was ligated to BglII cut plasmid pMA91.

The resultant ligation mix was used to transform E. Coli strain HB101 to ampicillin resistance. A colony of the transformed bacteria was isolated and was found to contain a plasmid exhibiting the predicted enzyme digestion pattern. The 5' end of the inserted DNA from this plasmid was sequenced and shown to have the anticipated sequence for a pre-μ cDNA.

(c) met-lambda (λ)

The met-λ DNA was cloned into the BglII site of plasmid pMA91. Plasmid pCT54 Clone 1 was cut with Hind III to the 3' side of the met-λ cDNA and this cleavage site was altered to a BcII site in a similar manner as previously described for pNP2. Following this the plasmid DNA was cut 5' of the λ gene at the BcII site and the resultant λ DNA was cloned into the BglII site of pMA91.

(d) Pre-lambda (λ)

Pre-λ cDNA was reconstructed into pMA 91 as follows. The plasmid pCT54 was digested with BcII and Hind III and the resultant vector DNA was isolated by gel electrophoresis and ligated together with two synthetic oligonucleotides, R162 and R163, and the two fragments from plasmid pAT λ 1-15.

R162 5' GATCAATGGCCTGGATT 3'

R163 5' GTGAAATCCAGGCCATT 3'

These fragments were produced by digesting pAT λ 1-15 with FokI and Hind III and isolating the 5'300 base pair FokI fragment and the 3' 600 base pair FokI-Hind III fragment by gel electrophoresis. The resultant ligation mixture was used to transform E. Coli strain HB101 to ampicillin resistance and a colony of bacteria containing a plasmid having the predicted correct restriction enzyme digestion pattern was isolated. The 5' end of the inserted DNA was sequenced and found to have the anticipated sequence of a pre-λ cDNA. This plasmid was digested with Hind III and the resultant Hind III cleaved ends converted to a BcII site by blunting with T4 polymerase and ligating with the linker R107. The resultant plasmid was then digested with BcII and the pre-λ cDNA isolated on a BcII fragment by gel electrophoresis. This BcII fragment was then ligated to BglI cut pMA91 to give a pMA 91 plasmid containing the full length pre-λ cDNA.

Expression of Immunoglobulin Genes in Yeast

The pMA91 derivative plasmids containing the pre-λ and pre-μ genes as prepared above were used to transform Saccharomyces cerevisiae yeast host organisms and the pre-λ and pre-μ genes were expressed by the transformed cells.

Saccharomyces cerevisiae strain MD46 when transformed with pMA91 pre-λ or pMA91 pre-μ gave rise to colonies which expressed immunoreactive proteins as revealed on Western blots. Yeast cells containing plasmid pMA91 pre-λ produced a protein which reacted with anti-λ antiserum and co-migrated on polyacrylamide gels with bacterially synthesised mature λ. Similarly yeast cells containing pMA 91 pre-μ produced a protein which reacted with anti-μ antiserum and co-migrated on polyacrylamide gels with bacterially synthesised mature λ protein. These observations indicate that both pre-μ and pre-μ are being processed to the corresponding mature proteins within the yeast host cell environment.

Additionally the λ protein product (but not the λ protein) was shown to be glycosylated. Cells were incubated in the presence or absence of tunicamycin at a concentration of 15 μg/ml. This compound specifically arrests the N-linked glycosylation of proteins. Cell extracts derived from cells incubated in the absence of tunicamycin showed higher molecular weight bands (as revealed by Western blotting) whilst extracts from cells incubated in the presence of tunicamycin showed no such higher molecular weight bands.

When cells were lysed with glass beads and the soluble and insoluble fractions examined it was found that the μ and λ proteins were exclusively in the insoluble fractions, as determined by Western blotting.

Secretion

After incubation transformed yeast cells were spun down and 1 ml volumes of supernatant were removed and passed through BSA-coated 0.2 μM Millipore filters to remove any remaining cellular material. ELISA assays for μ and λ protein were then carried out on the filtered supernatants. Only supernatants from pMA91 pre-λ harbouring cells showed detectable levels of immunoglobulin protein. Increased amounts of λ protein was detected in the supernatant when cells were grown in minimal medium to $OD_{660}=0.2$ and then spun down and resuspended in YPAB and harvested at $OD_{660}=1.0-1.5$. Thus the λ protein but not the μ protein is secreted from yeast cells.

Intracellular Location

After incubation cells containing pMA91 pre-μ were converted to spheroplasts and fixed in 5% acetic acid/95% ethanol (v/v) and incubated with fluorescein conjugated goat anti-mouse μ. The fixed cells were examined by fluorescent microscopy and the μ protein was found to be localised in the periphery of the spheroplasts and especially in vacuoles.

Expression of both μ and λ Proteins in the Same Cells

In order to express both genes in the same host cells it was necessary to provide compatible plasmids for use in transformation. The pre-λ gene was excised from pMA91 pre-λ on a Hind III fragment and inserted into the Hind III site of plasmid pLG89 (Griti L, and Davies J, Gene, 25 179-188, 1983). This plasmid contains a ura3 marker which can be used as a positive selection for transformed host cells. A convenient ura3 host organism is *S. cerevisiae* strain X4003-5B. Both plasmids, pMA91 pre-μ and pLG89 pre-λ, were transformed into this strain, and colonies were grown which contained together both the ura3 and leu2 markers. After incubation of the transformed cells both λ and μ proteins together were detected in the same cultures of X4003-5B using ELISA techniques. Levels of expression were comparable to those obtained for the individual genes in MD46 cells and for the λ gene alone in X4000-5B.

In addition, to check for assembly of the λ and μ proteins in vivo the following procedure was followd.

After the growth to an $OD_{660} \cong 1$, the transformed X4003-5B cell were spun down and resuspended in buffer, either 5 mM borate buffer at pH 8.0 or phosphate buffer at pH 5.8 either with or without detergent (e.g. 0.5% Triton X). The suspended cells were then lysed by vortexing with glass heads in buffer as above and the insoluble material was spun down. After centrifugation aliquots of the supernatant were assayed in a NIP binding assay (as described previously for assembled *E. Coli* μ and λ proteins). Specific antigen binding activity was detected in the supernatant and this activity was shown to be specifically competed out by free NIP (the specific antigen). These results indicated that μ and λ protein were expressed within the X4003-5 B cells and assembled into functional immunoglobulin molecules in vivo.

In the above experiments the culture medium used for incubating the transformed cells was yeast minimal medium (containing, per liter, 6.7 g DIFCO yeast nitrogen base without amino acids, 10 g glucose, and 200 mg each of histidine, tryptophan, methionine and adenine). When the λ protein alone was being expressed the medium contained in addition 200 mg/l of leucine, and when the μ protein alone was being expressed the medium contained in addition 200 mg/l of uracil.

We claim:

1. A process for producing an Ig molecule or an immunologially functional Ig fragment comprising at least the variable domains of the Ig heavy and light chains, in a single host cell, comprising the steps of:
    (i) transforming said single host cell with a first DNA sequence encoding at least the variable domain of the Ig heavy chain and a second DNA sequence encoding at least the variable domain of the Ig light chain, and
    (ii) independently expessing said first DNA sequence and said second DNA sequence so that said Ig heavy and light chains are produced as separate molecules in said transformed single host cell.

2. The process according to claim 1 wherein said first and second DNA sequences are present in different vectors.

3. The process according to claim 1 wherein said first and second DNA sequences are present in a single vector.

4. A process according to claim 2 wherein the or each vector is a plasmid.

5. A process according to claim 4, wherein the plasmid is col El, pcR1, pBR322, RP4 or phage DNA.

6. A process according to claim 1 wherein the host cell is a bacerium or a yeast.

7. A process according to claim 6, wherein the host cell is *E. Coli, B. subtilis* or *S. cerevisiae*.

8. A process according to claim 7, wherein the host cell is *E. Coli* strain HB101, X1776, X2887, PS410, MRC 1 RV308, B or E1035.

9. A process according to claim 1 wherein the Ig heavy and light chains are expressed in the host cell and secreted therefrom as an immunologically functional Ig molecule or Ig fragment.

10. A process according to claim 1 wherein the Ig heavy and light chains are produced in insoluble or membrane bound form and are solubilised and allowed to refold in solution to form an immunologically functional Ig molecule or Ig fragment.

11. A process according to claim 1, wherein the DNA sequences code for the complete Ig heavy and light chains.

12. A process according to claim 1, wherein said first or said second DNA sequence further encodes at least one constant domain, wherein the constant domain is derived from the same source as the variable domain to which it is attached.

13. A process according to claim 1, wherein said first or said second DNA sequence further encodes at least one constant domain, wherein the constant domain is derived from a source different from that from which the variable domain to which it is attached is derived.

14. A process according to claim 1, wherein said first and second DNA sequences are derived from one or more monoclonal antibody producing hybridomas.

15. A vector comprising a first DNA sequence encoding at last a variable domain of an Ig heavy chain and a second DNA sequence encoding at least a variable domain of an Ig light chain wherein said first DNA sequence and said second DNA sequence are located in said vector at different insertion sites.

16. A vector according to claim 15, which is a plasmid.

17. A host cell transformed with a vector according to claims 15.

18. A transformed host cell comprising at least two vectors, at least one of said vectors comprising a DNA sequence encoding at least a variable domain of an Ig heavy chain and at least another one of said vectors comprising a DNA sequence encoding at least the variable domain of an Ig light chain.

* * * * *